United States Patent [19]

Moay et al.

[11] Patent Number: 5,004,694
[45] Date of Patent: Apr. 2, 1991

[54] **COMPLEMENT-DEPENDENT CYTOLYTIC ANTI-*TRICHOMONAS VAGINALIS* MONOCLONAL ANTIBODIES**

[75] Inventors: Neomi Moay, Tel Aviv; Enrica Draghi, Rehovot, both of Israel

[73] Assignee: Interpharm Laboratories Ltd., Ness-Ziona, Israel

[21] Appl. No.: 93,431

[22] Filed: Sep. 4, 1987

[30] Foreign Application Priority Data

Sep. 5, 1986 [IL] Israel ......................... 79950

[51] Int. Cl.$^5$ .................. C12N 5/00; A61K 39/00
[52] U.S. Cl. .................. 435/240.27; 435/70.21; 435/172.2; 435/948; 424/85.8; 424/86; 424/87; 424/430; 530/387; 530/388; 530/808; 530/809; 935/110
[58] Field of Search ............... 435/7, 68, 172.1–172.3, 435/240.27, 948, 70.21; 424/85–87, 430, 85.8, 86, 87; 935/110; 436/548; 530/387, 388, 808, 809

[56] References Cited

FOREIGN PATENT DOCUMENTS 0141616 5/1985 European Pat. Off. .............. 435/68
0174874 3/1986 European Pat. Off. .............. 435/68
8602359 4/1986 PCT Int'l Appl. ..................... 435/7

OTHER PUBLICATIONS

Cooper, N., "The Complement System" in *Basic & Clinical Immunology*, 3rd ed., H. H. Fudenberg editor, pp. 83–95 (1980).
Biological Abstract 68(10): 60895.
Biological Abstract 64(11) 62897.
Torian et al., "Specific and Common Antigens of *Trichomonas vaginalis* Detected by Monoclonal Antibodies," *Infection and Immunity*, Jan. 1984, vol. 43, No. 1, pp. 270–275.
Connelly et al., "Identification of a Surface Antigen of *Trichomonas vaginalis*," *Infection and Immunity*, Aug. 1985, vol. 49, No. 2, pp. 270–274.
Alderete et al., "Monoclonal Antibody to a Major Surface Glycoprotein Immunogen Differentiates Isolates and Subpopulations of *Trichomonas vaginalis*," *Infection and Immunity*, Apr. 1986, vol. 52, No. 1, pp. 70–75.
Alderete et al., "Monoclonal Antibody to a Major Glycoprotein Immunogen Mediates Differential Complement-Independent Lysis of *Trichomonas vaginalis*," *Infection and Immunity*, Sep. 1986, pp. 697–699, vol. 53, No. 3.
Alderete, J., "Antigen Analysis of Several Pathogenic Strains of *Trichomonas vaginalis*," *Infection and Immunity*, Mar. 1983, pp. 1041–1047, vol. 39, No. 3.
Chang et al., "Monoclonal Antibodies Against *Trichomonas vaginalis*," *Hybridoma*, vol. 5, No. 1, 1986, pp. 43–51.
Hardy, R., "Complement Fixation by Monoclonal Antibody-Antigen Complexes," in Handbrook of Experimental Immunology, vol. 1, 4th edition, 1986, pp. 40.1–40.12.
Goding, J., Monoclonal Antibodies, Principles and Practice, 2nd edition, 1986, pp. 11–17 and 47–48 and 86–87.

*Primary Examiner*—Esther L. Kepplinger
*Assistant Examiner*—Carol A. Spiegel
*Attorney, Agent, or Firm*—Stephan P. Williams

[57] ABSTRACT

Novel monoclonal antibodies specific to *Trichomonas vaginalis*, having complement—fixing ability and lysing *Trichomonas vaginalis* in the presence of complement are disclosed and may be used in therapy and diagnosis of trichomoniasis. Hybridomas producing and compositions comprising these antibodies are also disclosed.

13 Claims, 6 Drawing Sheets

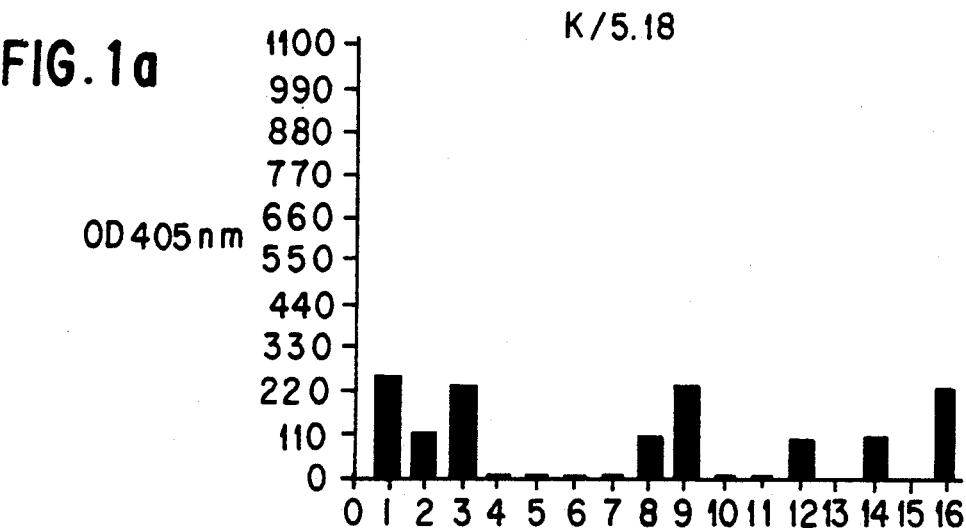
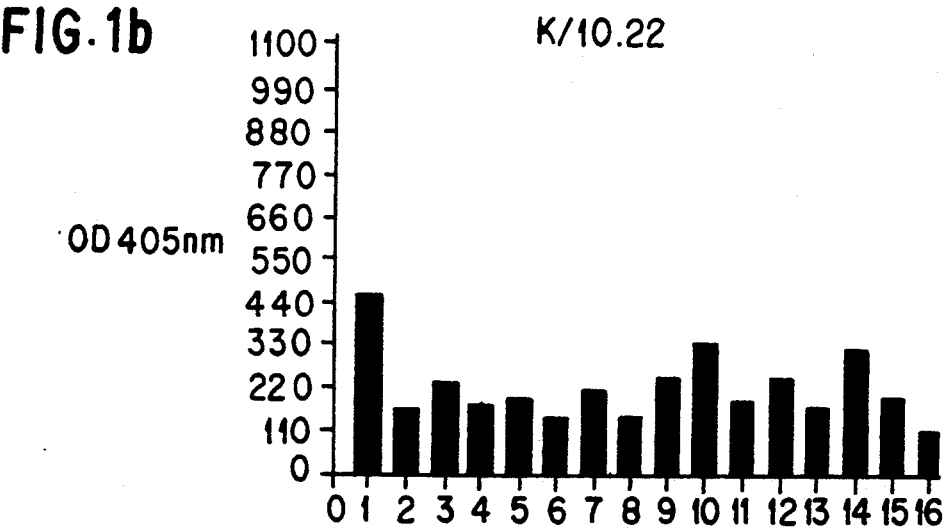
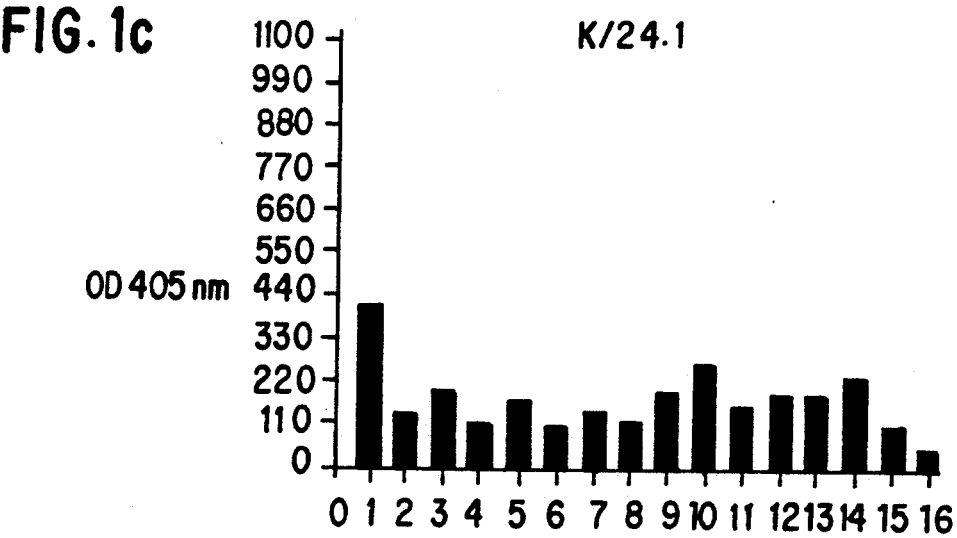

COMPLEMENT-DEPENDENT CYTOLYTIC ANTI-*TRICHOMONAS VAGINALIS* MONOCLONAL ANTIBODIES

FIELD OF INVENTION

The present invention relates to a monoclonal antibody specific to *Trichomonas vaginalis* having complement-fixing ability and capable of lysing *Trichomonas vaginalis* in the presence of a complement, to hybridomas producing said antibody and use thereof in immunotherapy and diagnosis.

BACKGROUND OF THE INVENTION

*Trichomonas vaginalis* is a parasitic protozoan, responsible for trichomoniasis, an infection of the urogenital tract which is one of the most common sexually transmitted diseases in the United States and in other parts of the world. Today, the treatment of trichomoniasis is based on the us of metronidazole and other nitroimidazole drugs, known to be carcinogenic in rodents, mutagenic in bacteria and teratogenic to the growing embryo and fetus. Pregnant women should not receive metronidazole, and in any case, it should not be given to patients over a long period of time. Moreover, it is known in the last years that metronidazole—resistant strains have emerged and this is a further reason to provide alternative means for the treatment of trichomoniasis.

In most cases, with proven trichomoniasis, high levels of antibodies to Trichomonas have been demonstrated. However, despite the fact that both humoral and cellular immune response can be demonstrated in these patients, protective immunity has not been effective and recurrent infections are very common. Attempts to stimulate the host's immune system against Trichomonas have been done by introducing a vaccine called Solco Trichovac, reported to be effective in the treatment of acute vaginal trichomoniasis and to be able to reduce the incidence of relapses. However, a vaccination plan is very costly and it requires repeated injections with only temporary efficiency.

In recent years, polyclonal antibodies (Alderete, J. F. 1983 Infect Immun. 39 1041-1047) as well as monoclonal antibodies (Torian B. E., Connelly, R. J., Stephens, R. S. and Stibbs, H. H. Infect. Immun. 1984, 43 270-275, Chang, T. H., Tsing, S. Y. and Tzeng, S. Hybridoma 1986, 5, 43-51), have been prepared against *Trichomonas vaginalis* in an attempt to study the antigenic nature of the parasite and to correlate it with its virulence.

In European Patent Application EP0141616, published on 24.10.85, monoclonal antibodies directed against *Trichomonas vaginalis* membrane protein antigens are disclosed and said to be useful in the purification and characterization of said membrane antigens, to facilitate studies on the vaccinogenic potential of said antigens and to he useful as diagnostic reagents for immunological assays for trichomoniasis infections.

In International Patent Application WO 86/02359 (PCT/GB 85/00470), published on 24.04.86, a monoclonal antibody specific for an antigen on species of Trichomonas is disclosed, mainly to be used in a labeled form in diagnosis. The monoclonal antibodies, including those directed against *Trichomonas vaginalis*, are also said to be useful in therapeutic compositions for the treatment of humans and/or animals, but no data on the lytic activity of the monoclonal antibodies is disclosed in order to support said affirmation.

In European Patent Application EP 0174874, published on 19.03.86, a monoclonal antibody specific for and cytolytic against *Trichomonas vaginalis* is disclosed and said to be useful in diagnosis or clinically for the prevention or treatment of trichomoniasis, when administered by oral route. It is very doubtful whether this monoclonal antibody administered by oral route will be useful at all for the treatment of trichomoniasis, since it will certainly be decomposed by proteolytic enzymes in the low pH vicinity of the stomach and will not reach the infection in the urogenital tract. Moreover, the monoclonal antibody is not sufficiently disclosed and Applicant's efforts to reproduce inherently cytolytic monoclonal antibody following the instructions given in said patent application have failed.

For all the above reasons there existed a real need for alternative means for treating trichomoniasis, a chronic disease which incidence is growing at a high rate in years. The present invention provides such alternative means in the form of monoclonal antibodies which by contact with the parasite would ensure the immediate lysis of Trichomonas without being negatively affected by the vaginal flora and/or the epithelial cells and which can be administered locally for treatment of trichomoniasis.

SUMMARY OF THE INVENTION

Many anti-*Trichomonas vaginalis* monoclonal antibodies were prepared and their lytic activity studied. Some of them, which did not fix complement, bound to *Trichomonas vaginalis*, but did not lyse it. Only those antibodies with complement fixing capacity were able to lyse live *Trichon.onas vaginalis* in the presence of complement. Without complement, they only agglutinate but do not lyse the microorganism. In contrast to the alleged inherent cytolytic activity of the prior art antibodies, the monoclonal antibodies of the present invention show complement-dependent cytolytic activity.

The present invention thus provides, for the first time, an anti-*Trichomonas vaginalis* monoclonal antibody which:

(i) has complement-fixing ability, and
(ii) lyses *Trichomonas vaginalis* in the presence of complement, but
(iii) agglutinates and does not lyse *Trichomonas vaginalis* in the absence of complement.

The present invention further provides hybridomas which produce a monoclonal antibody specific to *Trichomonas vaginalis*, with complement-fixing ability and complement-dependent cytolytic activity.

Another aspect of this invention is to provide methods for the production of said hybridomas and for the preparation of monoclonal antibodies from such hybridomas.

A further aspect of this invention is the use of the present monoclonal antibodies in prevention and/or therapy of trichomoniasis in mammals. To this end, there are provided pharmaceutical compositions comprising, together with a pharmaceutically acceptable carrier, a combination of the monoclonal antibody of the invention with an exogenous source of complement.

Any suitable source of complement can be used, such as human or animal serum. Guinea pig serum is preferred because it is more active as a source of complement than serum from other species, but rabbit serum may also be used. Diluted serum to the extent of losing its cytotoxicity to cells but keeping its complementary activity is preferably used in the combinations of the compositions of the invention, and these are shown herein to be effective against *Trichomonas vaginalis* both in culture and in cervico-vaginal secretions of women patients.

Mixtures of the monoclonal antibodies of the invention or mixture thereof with other anti-*Trichomonas vaginalis* monoclonal antibodies ("Antibody Cocktail") can be used in the compositions to increase the efficiency of the lytic process and to widen the range of the *Trichomonas vaginalis* strains susceptible to the antibodies.

The advantages of the suggested treatment over conventional treatments are as follows:

(1) Use is made of the unique qualities of monoclonal antibodies, namely: specifity, homogeneity, reproducibility and unlimited quantities of antibody.

(2) The suggested treatment is administered locally, and therefore is preferable to a systemic drug treatment, especially as the systemic treatment induces side effects, implies the danger of carcinogenicity and there is an increase in the number of drug-resistant strains.

(3) The cytotoxic effects of the antibodies and complement are directed specifically against *Trichomonas vaginalis* and therefore the local flora in the vagina should not be affected.

A further aspect of the invention is to provide a composition for the diagnosis of trichomoniasis comprising a monoclonal antibody of the invention and a diagnostically acceptable carrier. The ability of the different monoclonal antibodies to recognize different strains of Trichomonas can be used for diagnostic and identification purposes of the various Trichomonas strains, both for research and for medical use. Furthermore, an "Antibodies Cocktail" can be used in cases where a wide range of Trichomonas-recognition is required or when amplified recognition signals are needed. The fact that the monoclonal antibodies of the invention were prepared against a local *T. vaginalis* strain and at least one of the antibodies recognized 16 strains of an entirely different geographical area (U.S.A.) and from different sources implies that these antibodies may be used as a reliable tool in diagnosis.

Two of the hybridoma cell lines producing the novel antibodies were deposited with the Collection Nationale de Cultures de Microorganismes—CNCM, the Institut Pasteur. Paris, France, under the Budapest Treaty Deposit Procedure, on Sept. 1st 1986, under the accession numbers I-592 and I-593, for the cell lines designated TV K/518 and TV 1/315.10, respectively.

These and other aspects of the present invention will be better understood by reference to the following description, drawings and examples.

DETAILED DESCRIPTION OF THE INVENTION

Figure 1D:
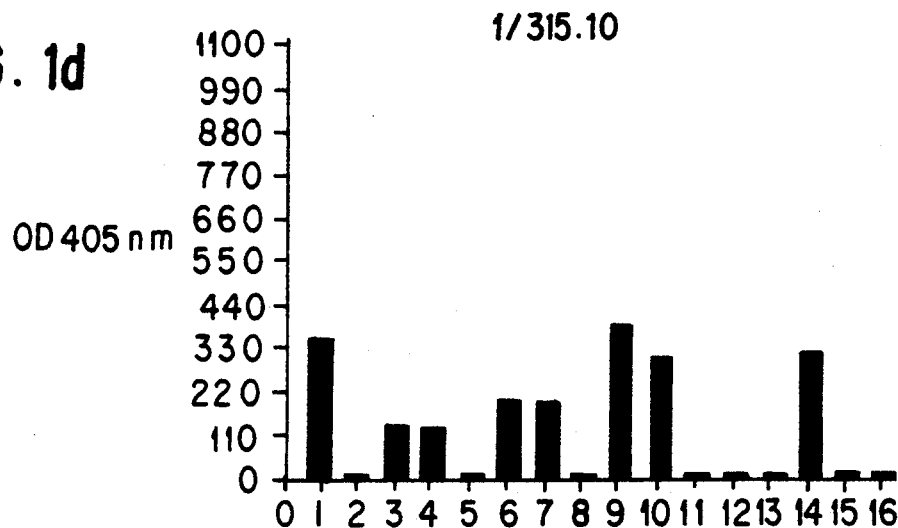
FIGS. 1(a-f) shows the binding patterns of six anti-*Trichomonas vaginalis* monoclonal antibodies to 16 strains of *Trichomonas vaginalis.*

The method of preparing the hybridoma comprises the following steps:

(a) Mice are immunized with live or with killed Trichomonas. The immunization schedule and the Trichomonas concentration should be such as to produce adequate titers of antibodies with pre-defined specificities. Three immunizations at 3-4 weeks' intervals with $2 \times 10^5$ living parasites or with $2 \times 10^6$ killed parasites have been found to be effective.

(b) The spleens of the immunized mice are removed and suspended in an appropriate medium, by well-known experimental techniques.

(c) The suspended spleen cells are fused with mouse myeloma cells with a suitable fusion promoter. The preferred ratio is 5-10 spleen cells per one myeloma cell. A total volume of about 0.5-1.0 ml of fusion medium is appropriate for about $10^8$ splenocytes. Any appropriate mouse myeloma cell line may be used. It should preferably be "drug resistant" so that unfused myeloma cells will not survive in a selective medium, while hybrids will survive. Most common are the 8-azaguanine resistant cell lines, which lack the enzyme hypoxanthine guanine phosphoribosyl transferase and will thus not be supported by HAT (hypoxanthine, aminopterin and thymidine) medium. The myeloma cell line used should preferably be of so-called "non-secreting" type, i.e., it should not by itself produce any antibody.

The preferred fusion promoter is polyethylene glycol having an average molecular weight from about 1000 to about 4000 (commercially available as PEG 1000, etc), preferably PEG 1000. However, other fusion promoters known in the art may be used. The mixture of unfused spleen cells, unfused myeloma cells, and fused cells are diluted and cultured in separate containers in a selective medium, e.g. HAT medium, which will not support the unfused myeloma cells, for a time sufficient to allow death of the unfused cells (about one week). The unfused spleen cells are non-malignant and have only a finite number of generations. Thus, after a certain period of time (about one week) they fail to reproduce. Only the fused cells continue to reproduce, because they have the malignant quality of the myeloma parent and the ability to survive in the selective medium.

(d) The supernatant in each container (well) containing a hybridoma is evaluated for the presence of antibody to Trichomonas.

(e) The hybridomas producing the desired antibody are selected and cloned.

(f) The monoclonal antibody may be produced from the hybridoma clones in one of two ways: either by culturing in vitro the hybridoma in a suitable medium for a suitable length of time and recovering the antibody from the supernatant, or by injecting the desired hybridoma into mice, thereby causing formation of antibody-producing tumors in the host mouse after a suitable incubation time, which will result in a high concentration of the desired antibody in the bloodstream and peritoneal exudate (ascites) of the host mouse, and recovering the desired antibody from the ascitic fluids of the host mouse by known techniques.

(g) Immunoglobulins of subtypes IgM, IgG$_2$ in mice, and in human also IgG$_3$ have the capacity to fix complement (Handbook of Experimental Immunology, Third Edition, Volume 3, D. M. Weir Editor, Blackwell 1978 Chapter 5A). However, monoclonal antibody might differ in this respect from polyclonal antibodies; some monoclonal antibodies of the IgG$_2$ subtype might not fix complement and some IgG$_3$ monoclonal antibodies of mouse origin, which usually do not fix complement, might do so.

The novel monoclonal antibodies produced by hybridomas No. TV K/5.18 and TV 1/315.10 have been found to belong to immunoglobulins IgM and IgG3 subtypes, respectively. Other monoclonal antibodies produced for comparison belong to IgG1 subtype.

(h) The complement-fixing property of the antibodies produced by clones No. TV K/5.18 and No. TV 1/315.10, and their ability to induce complement-dependent lysis of living Trichomonas in presence of complement can be utilized for immunotherapy of trichomoniasis. It is suggested to administer locally, i.e., intravaginally to patients suffering from trichomoniasis, a combination of said antibody and complement together with a pharmaceutically acceptable carrier. A lysis in situ of the Trichomonas will occur.

In fact, preliminary experiments have demonstrated that cervico-vaginal secretions obtained from women did not inhibit the lytic activity of the antibody with the complement (Table 5).

(i) In order to test the effectiveness of the antibodies to be used for immunotherapy, a sensitivity test can be done on an individual basis. A sample containing the Trichomonas can be taken from the prospective patient and be mounted on a microscopic slide. A binding assay can be run on this specimen using a mixture of the antibodies of the present invention, in order to test whether the antibody recognizes the correspondent *Trichomonas vaginalis* strain. The lytic process will be effective and the treatment successful, only when the antibody recognizes the Trichomonas strain, as indicated by a positive binding assay.

The following examples illustrate the preferred embodiments of the invention without limiting the scope thereof.

EXAMPLE 1

Production of monoclonal antibodies

A. Immunization and somatic cell hybridization: Female Balb/c mice (Tel-Aviv University animal breeding facilities of the Sackler Medical School, Tel-Aviv, Israel) were immunized either with live *Trichomonas vaginalis* or with killed parasites. The immunization protocol with live Trichomonas was as follows: $2 \times 10^5$ freshly washed parasites were injected intraperitoneally into the mice 3 times at 3 weeks intervals. When killed Trichomonas were used similar protocol was used except that $2 \times 10^6$ frozen and thawed parasites were used. One month after the last immunization the mice were injected intravenously with $2 \times 10^6$ killed parasites. Three days later spleens were removed and cells extracted for cell fusion. The fusion with NSO myeloma cells was carried out according to the procedure described by Kennett et al (Kennett R. H., Denis, K. A., Tung, A. S. and Klinman, N. R. 1978, Curr. Top. Microbiol. Immunol. 81, 77). About $1 \times 10^8$ spleen cells were fused with $1 \times 10^7$ NSO myeloma cells using 33% polyethylene glycol (Baker 1000).

B. Selection and growth of hybridoma:

After cell fusion the cells were cultured in HAT medium (hypoxanthine, aminopterin and thymidine) at 37 deg C. in a humid atmosphere of 10% $CO_2$ and air. About 2 weeks later supernatants from wells containing growing hybridomas were collected and tested for antibody binding capacity to *Trichomonas vaginalis* using the enzyme-linked-immunosorbent-assay (ELISA) as follows:

50 micro liters of freshly washed or frozen *Trichomonas vaginalis* at a concentration of $2.5 \times 10^6$ cells/ml were dispensed into flat bottom microtiter plates. Lyophilized Trichomonas strains were diluted to a concentration of 10 micrograms/ml protein in 0.05M carbonate buffer pH 9.6. 100 micro liters of suspensions were dispensed into individual wells and allowed to stand overnight at room temperature for coating. The plates were then washed 3 times with distilled water to remove the carbonate buffer and unbound antigens. The plates were then either fixed with 80% acetone by adding 50 microliters into each well and allowing to dry, or, if no fixation was performed, the plates were washed 3 times with washing buffer (PBS containing 0.1% TWEEN-20) and kept at $-20$ deg C. for several weeks until used. Before use the plates were washed once more with distilled water. 200 microliters of 0.5% gelatine in PBS were added to each well. The plates were incubated for at least 1 hour at 37 deg C. and the liquid was discarded. Undiluted culture supernatants or appropriately diluted murine ascitic fluid (100 micro liters) were added to each well. Plates were incubated for at least 1 hour at 37 deg C. The supernatants were then discarded and the plates were washed 5 times with washing buffer (PBS containing 0.1% TWEEN-20). 100 micro liters per well of goat anti-mouse F(ab)$_2$ alkaline phosphatase conjugate were added and the plates were incubated for 1 hour at 37 deg C. The unbound conjugate was then discarded and the plates washed 5 times with washing buffer. 100 microliters of the substrate p-nitrophenyl phosphate at 1 mg/ml in 10% diethanolamine buffer, pH 9.8 containing 2 mM $MgCl_2$ were added into each well. After 10 minutes incubation at 37 deg C. the developed color is read spectrophotometrically at 405 nm using Micro-Elisa Dynatec automatic reader.

For production of larger quantities of antibodies, $2 \times 10^6$ hybridoma cells were injected intraperitoneally into Balb/c mice primed with 2, 6, 10, 14 —tetramethyl—pentadecane (Pristane, Aldrich Chemical Co.). The ascitic fluids produced by these mice contained high concentrations of the desired antibodies and were used to characterize the antibodies.

EXAMPLE II

Screening and isolation of hybridomas producing monoclonal antibodies to *Trichomonas vaginalis*:

Three hybridizations were performed by fusion of NSO myeloma cells and lymphocytes from Balb/c mice immunized with *Trichomonas vaginalis*. The spleen cells for two fusion were obtained from mice immunized with live Trichomonas and the spleen cells for one fusion were obtained from a mouse immunized with killed Trichomonas. Colonies were observed in almost all the wells. Supernatants from these cultures were screened for their binding capacity to a clinical isolate of *Trichomonas vaginalis*. 454 hybridomas were found to be positive. Some of these hybridoma lines subsequently died or ceased to produce antibodies. 48 of the hybridomas were cloned for further studies using the limited dilution procedure.

Binding patterns of anti-*Trichomonas vaginalis* monoclonal antibodies to acetone-fixed and to non-fixed Trichomonas strains hybridomas secreting anti-*Trichomonas vaginalis* monoclonal antibodies to various Trichomonas strains were analyzed. The Trichomonas strains in the microtiter plates were either non-fixed or acetone-fixed FIGS. 1(a-f) and 2(a-f) illustrate the binding patterns of monoclonal antibodies produced from clones K/5.18, 1/315.10, K/10.22, K/14.2, K/24.1 and K/71-2 to the following *Trichomonas vaginalis* strains:

| 1. | Clinical isolate of *Trichomonas Vaginalis*. | | | | |
|----|------|----|-------|-----|--------|
| 2. | 30001 | 7. | 30245 | 12. | 0783/1 |
| 3. | 30184 | 8. | 30092 | 13. | 0783/2 |
| 4. | 30185 | 9. | 0683/2 | 14. | 0783/3 |
| 5. | 30188 | 10. | 0683/3 | 15. | SSH-1000 |
| 6. | 30236 | 11. | 0683/4 | 16. | and *Trichomonas gallinae* 30095 |

The Binding assay was performed using the ELISA assay as described in Example 1B above. The intensity of the color is proportional to the binding capacity.

Figure 1E:
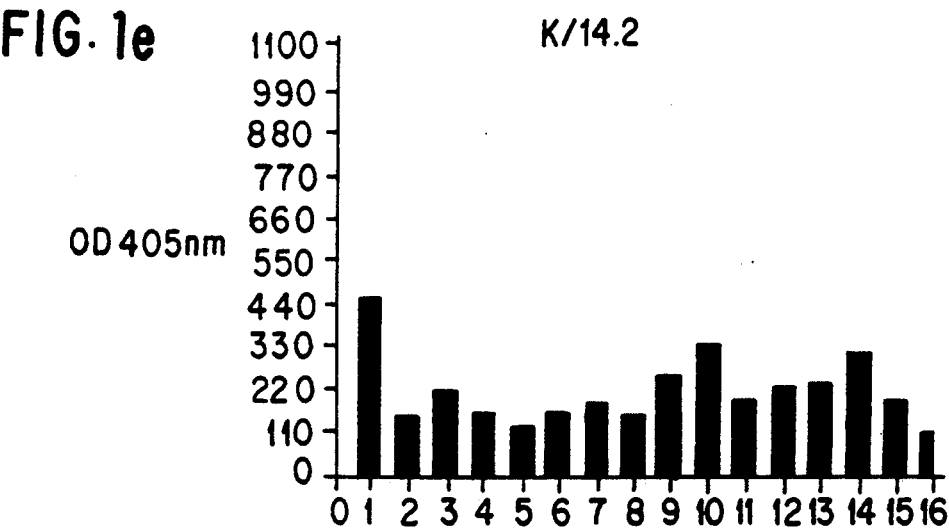
Figure 1F:
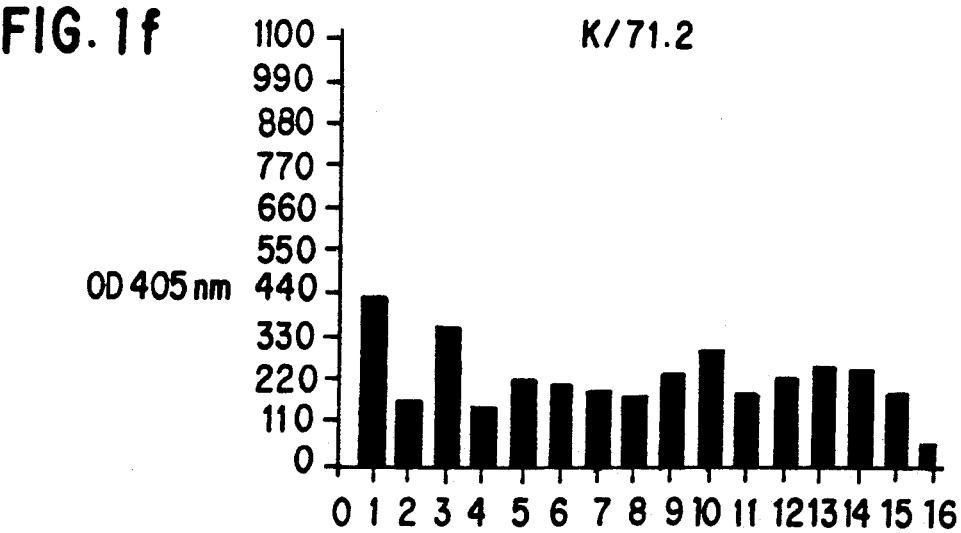
Figure 2A:
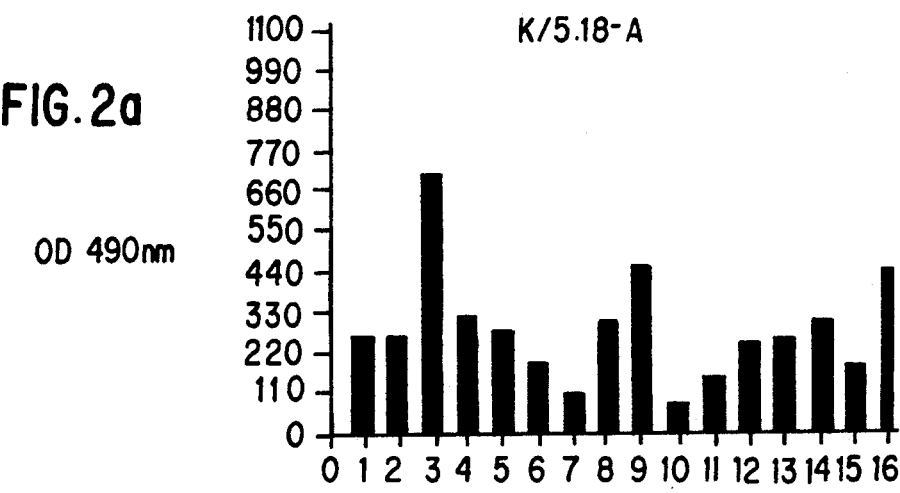
FIGS. 2(a-f) shows the binding patterns of six anti-*Trichomonas vaginalis* monoclonal antibodies to 16 acetone-fixed strains of Trichomonas.
Figure 2B:
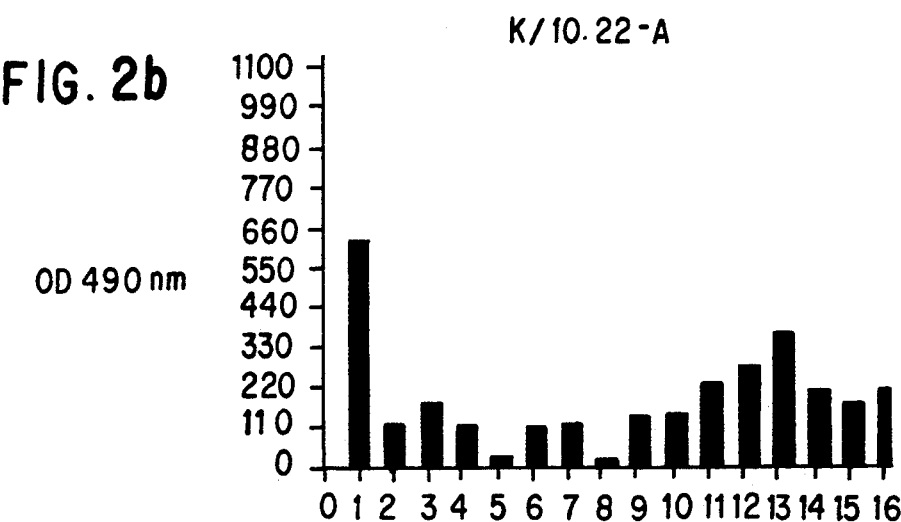
Figure 2C:
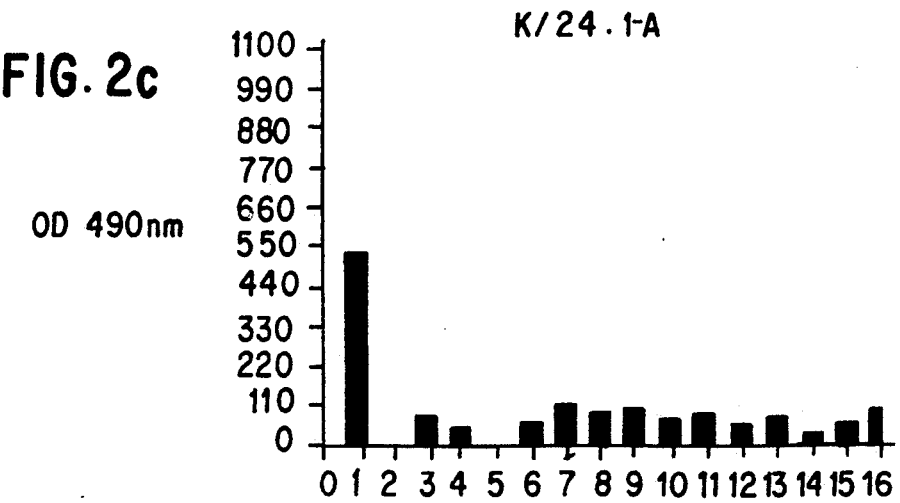
Figure 2D:
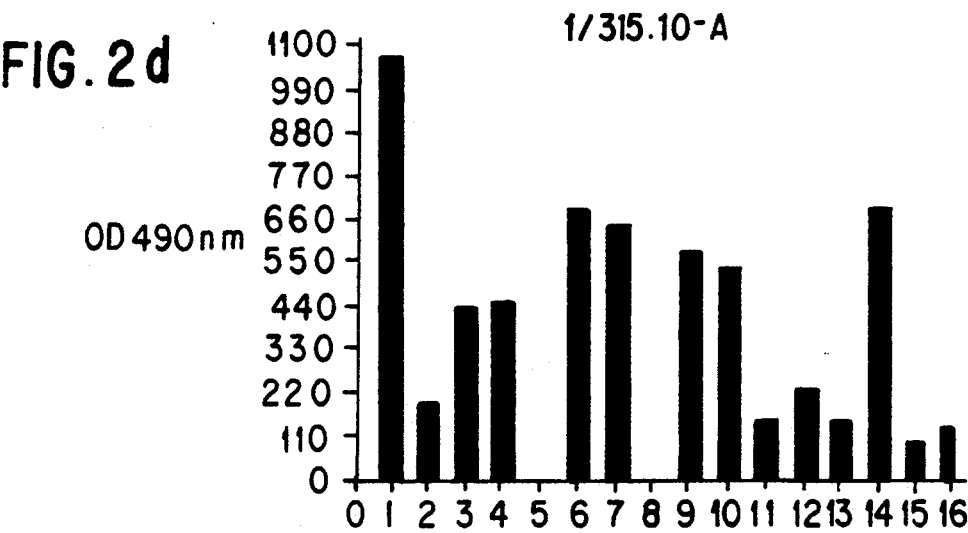
Figure 2E:
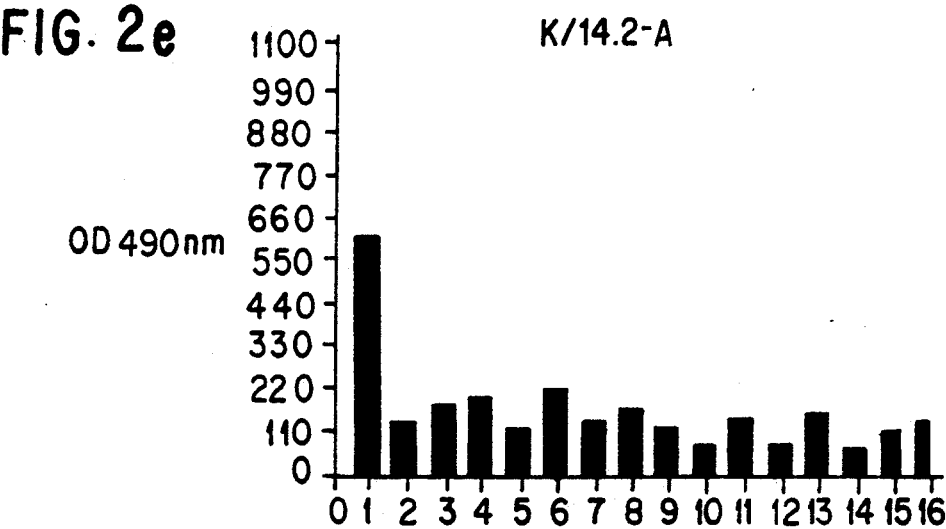
Figure 2F:
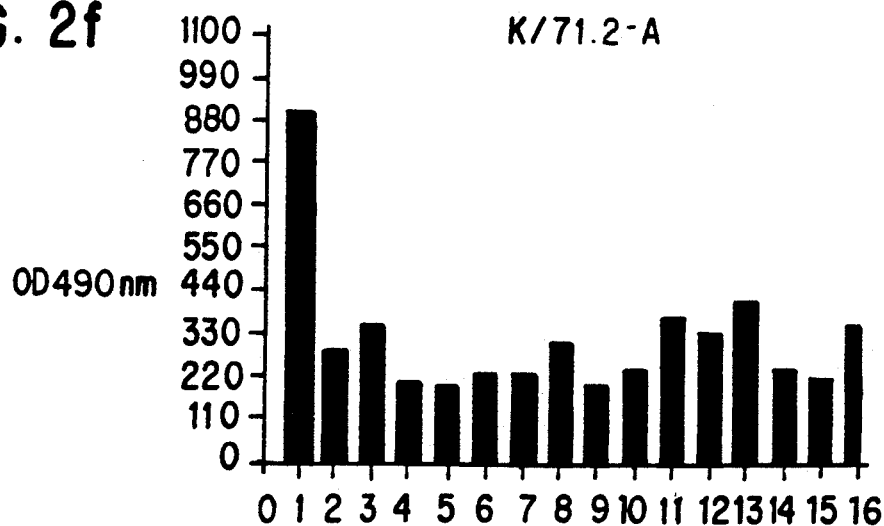

In FIG. 2 are illustrated the binding patterns of monoclonal antibodies produced from the same hybridoma clones as in FIG. 1, to acetone-fixed strains of *Trichomonas vaginalis*. The protocol of the experiment described before, was modified to include the following:

(a) The Trichomonas bound to the wells, were fixed with 50 micro liters of 80% acetone which was allowed to dry in the wells.

(b) Goat anti-mouse F(ab)$_2$ coupled to horseradish peroxidase was used as second antibody instead of alkaline phosphatase in FIG. 1 and the substrate was o-phenylenediamine (OPD). The color was read at 490 nm.

A comparison of the binding patterns of the monoclonal antibodies to acetone-fixed (FIG. 2(a-f)) and to non-fixed-Trichomonas strains (FIG. 1(a-f)) showed the following:

1. Acetone fixation, in general, enhances the binding capacity of the antibody to pre-existing antigenic determinants. (see FIG. 1a, K 5/18, Nos. 2, 3, 8, 9, etc and FIG. 1d, 1/315.10, Nos. 1, 3, 4, 6, 7, etc).

2. Acetone fixation reveals masked antigenic determinants on Trichomonas strains which were not recognized by the antibody without the fixation. (FIG. 1a, K 5/18, Nos. 4, 5, 6, 7, etc).

EXAMPLE III

Isolation and growth of *Trichomonas vaginalis*:

A strain of *Trichomonas vaginalis* was isolated from a patient attending the Gynecology Clinic, Zamenhoff Medical Center, Tel-Aviv, Israel. It was cultured in tissue culture flasks at 37 deg C. in TY-S-33 medium containing:

| 2 gr | Yeast extract |
|------|---------------|
| 4 gr | Bacto-peptone or trypticase |
| 2 gr | Glucose |
| 400 mg | NaCl |
| 262 mg | K$_2$HPO$_4$.3H$_2$O |
| 120 mg | KH$_2$PO$_4$ |
| 200 mg | L-Cysteine-HCl |
| 40 mg | Ascorbic acid |

-continued

| 4.5 mg | Ferric ammonium acetate |
|--------|-------------------------|

All these ingredients were dissolved in 174 mls of distilled water and 20 mls of inactivated horse serum were added. The media was sterilized by filtration.

Other strains of *Trichomonas vaginalis*, to be used for characterization of the monoclonal antibodies were obtained in lyophilized form from Serono Diagnostics, Boston, Mass. U.S.A. See following strain Nos.:

| 30001 | 30245 | 0783/1 |
|-------|-------|--------|
| 30184 | 30092 | 0783/2 |
| 30185 | 0683/2 | 0783/3 |
| 30188 | 0683/3 | SSH-1000 |
| 30236 | 0683/4 | 30095 |

EXAMPLE IV

Characterization of monoclonal antibodies' immunoglobulins subtypes.

Double immunodiffusion in 1% agar (special Noble agar, Difco), was performed according to the procedure of Ouchterlony (Ouchterlony, O. 1948, Acta, Pathol. Microbiol Scand. 25, 186–191).

The supernatant fluids from the hybridomas were tested against goat anti-mouse immunoglobulins IgM, IgG$_1$, IgG$_2$a, IgG$_2$b, IgG$_3$, and IgA (Litton Bionetics, Kensington, Md. U.S.A.). Diffusion was allowed to take place for 24–36 hrs, after which the precipitation lines were observed. The results are summarized in Table No. 1 hereinafter. It is interesting to note that out of 20 clones tested for their Ig subtypes, 6 produced IgG3. All IgG3 producing clones resulted from hybridization of splenocytes of mice immunized with live *Trichomonas vaginalis*.

TABLE 1

IMMUNOGLOBULIN SUBTYPES OF ANTI-*TRICHOMONAS VAGINALIS* MONOCLONAL ANTIBODIES

| Clone No. | Ig subtype | Clone No. | Subtypes |
|-----------|-----------|-----------|----------|
| 1/25.5 | IgG3 | 2/32.26 | IgG3 |
| 1/315.10 | IgG3 | 2/46.10 | IgG3 |
| 1/630.21 | IgG3 | 2/634.3 | IgG1 |
| 1/476.3 | IgM | | |
| | | K/71.2 | IgG1 |
| 2/10.22 | IgG1 | K/24.1 | IgG1 |
| 2/117.3 | IgG1 | K/10.22 | IgG1 |
| 2/37.5 | IgG1 | K/5.18 | IgM |
| 2/52.2 | IgG3 | K/89.1 | IgG1 |
| 2/647.3 | IgG3 | K/95.12 | IgG1 |
| 2/473.23 | IgG1 | K/14.2 | IgG1 |

EXAMPLE V

Purification of anti-*Trichomonas vaginalis* monoclonal antibodies: binding capacity and complement dependent cytotoxicity.

Ascitic fluids were obtained from Balb/c mice inoculated with hybridoma cells—clones No. TV K/5.18 and No. TV 1/315.10. The immunoglobulin fractions were isolated using the following methods:

(1) Precipitation of immunoglobulins with 50% (NH$_4$)$_2$SO$_4$, pH 8.0 and dialyzing them against PBS for 24 hours at 4 deg C.

(2) Precipitation of IgM by dialysis of ascitic fluid against distilled water for 24 h at 4 deg C. and dissolving the precipitate in PBS containing 0.2 M NaCl.

(3) Binding the specific antibody to a column of sepharose-protein A at pH 7.2 (in PBS) and eluting the antibody using the following buffers:
0.1 M phosphate buffer pH 6.0
0.1 M phosphate buffer pH 5.0
0.2 M acetate buffer pH 4.0
0.2 M glycine buffer pH 3.0

(4) Gel filtration of the ascitic fluid on SEPHACRYL columns S-300.

Figure 3:
FIG. 3 shows the polyacrylamide gel electrophoresis of the partially purified anti-Trichomonas monoclonal antibodies (clones No. TV 1/315.10 and No. TV K/5.18).

The purity of the antibodies obtained by the various purification techniques was determined by running the material on poly-acrylamide gels (Laemmli U.K., 1970, Nature 227, 680–685), as illustrated in FIG. 3.

Purified antibodies were tested for their binding activity to Trichomonas (using the ELISA technique), and for their ability to lyse Trichomonas in presence of complement.

In Table 2 are summarized the results of the binding activities and the complement-dependent lytic activities of crude and partially purified monoclonal antibodies clones No. TV K/5.18 and No. TV 1/315.10. It can be seen that clone No. TV K/5.18 produces a more labile antibody than TV 1/315.10, and it could lose complement-dependent lytic activity during the purification steps.

and IgG$_3$ respectively. Their ability to lyse Trichomonas in presence of complement was tested, using the following procedure:

In flat bottom wells of microtiter plates, a mixture was prepared with the following ingredients:
20 microliters of $2 \times 10^6$/ml cultured *Trichomonas vaginalis*
20 microliters of various dilutions of antibodies in PBS
20 microliters of diluted normal guinea-pig or rabbit serum as a source of complement
60 microliters of PBS The plates with the reaction mixtures were incubated for 30 min. at 37 deg C. and each well was then observed microscopically for lysis.

A monoclonal antibody to a non-related substance i.e. alpha-feto protein (clone No. 263.1), was used as negative control. It neither binds to the Trichomonas nor lyses it. Therefore, it can be concluded that the lytic process requires:
(a) Antigenic recognition by the antibody.
(b) Complement-fixation capacity of the antibody.
(c) Addition of complement.

Table 3—illustrates the binding capacity of various monoclonal antibodies to Trichomonas and the ability of clones No. TV K/5.18 and TV 1/315.10 to fix-complement and thus induce lysis of Trichomonas.

TABLE 2

BIOLOGICAL ACTIVITIES OF CRUDE AND PARTIALLY PURIFIED MONOCLONAL ANTIBODIES TO TRICHOMONAS (CLONE K/5.18 AND 1/315.10)

| | Clone 1/315.10 | | | | | Clone K/5.18 | | | | |
|---|---|---|---|---|---|---|---|---|---|---|
| | Binding Activity (ELISA) | | Complement-Dependent Cytotoxicity[4] | | | Binding Activity (ELISA) | | Complement-Dependent Cytotoxicity[4] | | |
| | | | | Lysis of Trichomonas | | | | | Lysis of Trichomonas | |
| Form of Antibody | Dilution of Antibody | OD at 490 nm | Dilution of Antibody | with c' | w/o c' | Dilution of Antibody | OD at 490 nm | Dilution of Antibody | with c' | w/o c' |
| Ascitic Fluid | $10^{-2}$ | 0.423 | 1:10 | 0 | 0 | 1:10 | 0.475 | 1:10 | +++ | 0 |
| | $10^{-3}$ | 0.313 | 1:100 | 0 | 0 | 1:50 | 0.452 | 1:100 | +++ | 0 |
| | $10^{-4}$ | 0.260 | 1:200 | +++ | 0 | 1:100 | 0.432 | 1:200 | +++ | 0 |
| | $10^{-5}$ | 0.018 | 1:400 | +++ | 0 | 1:500 | 0.123 | 1:400 | ++ | |
| | $10^{-6}$ | 0.004 | 1:800 | +++ | 0 | 1:1000 | 0.041 | 1:800 | + | |
| | | | 1:1600 | ++ | 0 | | | | | |
| Tissue Culture Supernatant | 1 × | 0.403 | 1 × | +++ | 0 | N.D. | | N.D. | | |
| | $10^{-1}$ | 0.249 | 1:2 | +++ | 0 | | | | | |
| | | | 1:5 | +++ | 0 | | | | | |
| | | | 1:10 | +++ | 0 | | | | | |
| | | | 1:50 | +++ | 0 | | | | | |
| Ammonium Sulphate Precipitate[1] | 1 × | 0.319 | 1:10 | 0 | 0 | 1 × | 0.916 | 1:20 | 0 | 0 |
| | $10^{-1}$ | 0.367 | 1:100 | +++ | | 1:10 | 0.555 | 1:40 | 0 | |
| | $10^{-2}$ | 0.416 | 1:500 | +++ | | 1:100 | 0.297 | 1:80 | 0 | |
| | $10^{-3}$ | 0.325 | | | | | | 1:160 | 0 | |
| H$_2$O Precipitate[2] | N.D. | | 1:2 | ++ | 0 | N.D. | | 1:2 | 0 | 0 |
| | | | 1:10 | +++ | 0 | | | 1:10 | 0 | 0 |
| | | | 1:50 | +++ | 0 | | | 1:50 | 0 | 0 |
| | | | 1:100 | ++ | 0 | | | | | |
| | | | 1:500 | + | | | | | | |
| | | | 1:1000 | + | | | | | | |
| Sephacryl S-300[3] | 1 × | 0.714 | 1:10 | ++ | 0 | 1 × | 0.823 | 1 × | ++ | 0 |
| | $10^{-1}$ | 0.647 | 1:50 | ++ | 0 | 1:10 | 0.487 | 1:10 | ++ | 0 |
| | $10^{-2}$ | 0.579 | | | | 1:100 | 0.044 | | | |

[1]Protein concentrations of clones 1/315.10 and K/5.18 were 4.4 mg/ml and 5.2 mg/ml respectively.
[2]Protein concentration of clones 1/315.10 and K/5.18 were 0.658 mg/ml and 3.62 mg/ml respectively.
[3]Protein concentrations of the eluted peak fractions of clones 1/315.10 and K/5.18 were 0.54 mg/ml and 0.9 mg/ml respectively.
[4]+++ >90% lysis
++ 60%–80% lysis
+ 40%–60% lysis
± 20%–40% lysis
0 No lysis

EXAMPLE VI

Complement-dependent cytotoxicity:

The lytic process is complement-dependent and is triggered by the binding of the antibody to its corresponding antigen. Clones No. TV K/5.18 and No. TV 1/315.10 belong to the immunoglobulin subtypes IgM

TABLE 3

BIOLOGICAL ACTIVITIES OF ANTI-TRICHOMONAS VAGINALIS MONOCLONAL ANTIBODIES

| Clone No. | Binding Activity (ELISA) Dilution of McAb | O.D. at 490 nm | C' Dependent Cytotoxicity Dilution of McAb | Lysis of T.V. |
|---|---|---|---|---|
| K/5.18 (Ascitic fluid) | 1:10 | 0.504 | 1:10 | +++ |
|  | 1:50 | 0.445 | 1:20 | +++ |
|  | 1:100 | 0.423 | 1:40 | +++ |
|  | 1:500 | 0.129 | 1:100 | ++ |
|  | 1:1000 | 0.041 | 1:200 | ++ |
|  | 1:5000 | 0.060 | 1:500 | ++ |
| No. 1/315.10 (Ascitic fluid) | $10^{-2}$ | 0.701 | 1:10 | Immobilization |
|  | $10^{-3}$ | 0.603 | 1:100 | zation |
|  | $10^{-4}$ | 0.200 | 1:200 | +++ |
|  | $10^{-5}$ | 0.036 | 1:400 | +++ |
|  | $10^{-6}$ | 0.011 | 1:800 | +++ |
| No. K/10-22 (Ascitic fluid) | $10^{-2}$ | 0.183 | 1:10 | + |
|  | $10^{-3}$ | 0.152 | 1:50 | 0 |
|  | $10^{-4}$ | 0.150 | 1:100 | 0 |
|  | $10^{-5}$ | 0.060 | 1:500 | 0 |
|  | $10^{-6}$ | 0.007 |  |  |
| K/71.2 (Ascitic fluid) | $10^{-2}$ | 0.226 |  |  |
|  | $10^{-3}$ | 0.219 | 1:10 | + |
|  | $10^{-4}$ | 0.191 | 1:50 | ± |
|  | $10^{-5}$ | 0.096 | 1:100 | 0 |
|  | $10^{-6}$ | 0.019 | 1:500 | 0 |
| K/14.2 | $10^{-2}$ | 0.462 | 1:10 | 0 |
|  | $10^{-3}$ | 0.290 | 1:50 | 0 |
|  | $10^{-4}$ | 0.110 | 1:100 | 0 |
|  | $10^{-5}$ | 0.037 | 1:500 | 0 |
|  | $10^{-6}$ | 0.003 |  |  |
| K/24.1 | $10^{-2}$ | 0.201 | 1:10 | + |
|  | $10^{-3}$ | 0.200 | 1:50 | ± |
|  | $10^{-4}$ | 0.115 | 1:100 | 0 |
|  | $10^{-5}$ | 0.036 | 1:500 | 0 |
|  | $10^{-6}$ | 0.013 |  |  |
| anti alpha feto protein clone No. 263.1 | $10^{-1}$ | 0.004 | 1:10 | 0 |
|  | $10^{-2}$ | 0.005 | 1:50 | 0 |
|  |  |  | 1:100 | 0 |
|  |  |  | 1:500 | 0 |

Legend of Table 3:
+++ >90% lysis
++ 60-80% lysis
+ 40-60% lysis
± 20-40% lysis
0 no lysis

EXAMPLE VII

Titration to determine non-toxic complement The serum used as a source for complement, when used undiluted, could be cytotoxic to the cells. Therefore, each batch of serum, was titrated in order to determine the levels of its toxic and its complementary activities as demonstrated in the following Table 4. The selected serum dilution used in the complement dependent - cytotoxic assay was such that only the complementary activity was demonstrated.

Figure 4A:
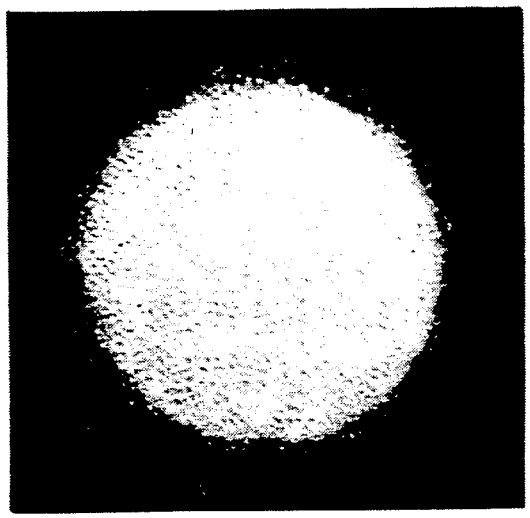
FIGS. 4(a-c) shows the effect of anti-*Trichomonas vaginalis* monoclonal antibody on *Trichomonas vaginalis* with and without complement.
Figure 4B:
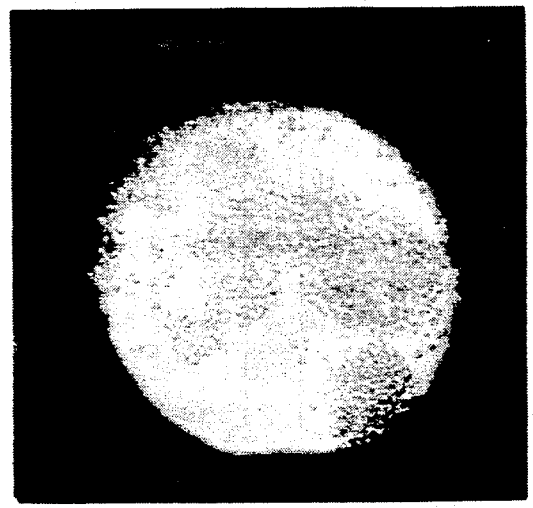
Figure 4C:
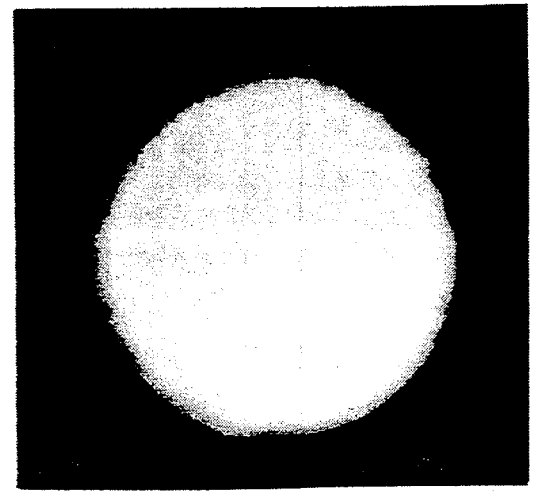

The complement-dependent cytolytic effect of monoclonal antibody TV K/5.18 on Trichomonas is well illustrated in FIGS. 4 (a)–(c) in which (a) illustrates a control (incubation with PBS), (b) illustrates agglutination (incubation with TV K/5.18 without complement), and (c) illustrates lysis (incubation with TV K/5.18 with complement). It can be seen that in absence of complement from the system, the antibody does no lyse the Trichomonas; instead the Trichomonas is being agglutinated.

TABLE 4

Titration for Toxic and Complementary Activities of Complement

| Toxic Activity of Complement | | Clone 1/315.10 Complementary Activity of Complement | | | |
|---|---|---|---|---|---|
| Dilution of G.P.C. | Lysis of Trichomonas Vaginalis W/O Antibody | Dilution of Antibody | Lysis of Trichomonas Vaginalis | | |
|  |  |  | With C' 1:4 | With C' 1:8 | W/O C' |
| 1:2 | +++ | 1:2 | +++ | +++ | 0 |
| 1:4 | + | 1:10 | ++ | ++ | 0 |
| 1:8 | 0 | 1:50 | ++ | + | 0 |
|  |  | 1:100 | + | 0 | 0 |
|  |  | 1:200 | + | 0 | 0 |

EXAMPLE VIII

Effect of cervico-vaginal secretions on the complement-dependent cytolytic activity of a mixture of monoclonal antibody (clone No. TV K/5.18) and complement.

In order to examine the possibility that cervico-vaginal secretions obtained from patients might inhibit (or enhance) the lytic activity induced by a mixture of monoclonal antibody and complement, the following experiment was performed;

A mixture of 20 microliters of $2\times10^6$/ml cultured Trichomonas vaginalis, 20 microliters of anti-Trichomonas vaginalis monoclonal antibody (clone No. K/5.18 from ascitic fluid diluted 1:2), 20 microliters of complement (rabbit or guinea pig serum diluted 1:3 as a source of complement). and 60 microliters of cervico-vaginal secretions (obtained from women patients of Gynecology Clinic, Zamenhoff Medical Center, Tel-Aviv, Israel), was incubated for 30 min at 37 deg C. in flat bottom microtiter plates. Lysis of Trichomonas was observed microscopically. The results are summarized in Table No. 5 and it can be seen that the cervico-vaginal secretions did not inhibit the lytic activity of the antibody-complement mixture under these experimental conditions.

TABLE 5

EFFECT OF CERVICO-VAGINAL SECRETIONS ON COMPLEMENT-DEPENDENT CYTOLYTIC ACTIVITY OF MONOCLONAL ANTIBODY (CLONE K/5.18) ON TRICHOMONAS VAGINALIS

| Patient No. | pH of Secretions | % LYSIS Cervico-vaginal secretion | |
|---|---|---|---|
|  |  | 20'/37 deg C. + Ab + C' | 40'/37 deg C. + Ab + C' |
| 1. | 5.0 | 90 | 90 |
| 2. | 5.0 | 70 | 90 |
| 3.* | 7.0 | 70 | 90 |
| 4 | 6.0 | 100 | 100** |
| 5. | 7.0 | 95 | 95 |
| 6. | 5.0 | 60 | 80 |
| 7. | 5.0 | 100 | 100** |
| 8. | 6.5 | 100 | 100** |
| 9. | 5.5 | 70 | 90 |
| 10. | 6.0 | 80 | 90 |
| 11. | 6.5 | 80 | 80 |
| 12. | 6.5 | 80 | 90 |
| 13. | 7.0 | 80 | 90 |
| 14. | 6.5 | 80 | 90 |

*positive for T.V.
**total lysis, no traces of the T.V.

COMPOSITIONS

The monoclonal antibodies of the present invention may be formulated together with an exogenous source of complement and a pharmaceutically acceptable carrier into compositions to be used for local treatment of trichomoniasis. Any suitable form of composition which can be administrated locally is contemplated by the present invention. Compositions for intravaginal application are preferred, e.g.. vaginal suppositories vaginal tablets, tampons, lyophilized vials to be reconstituted into a douche or any other suitable form for intravaginal administration. Also formulations for topical use, e.g., jelly, spray, cream or ointment may be considered for the disinfection of the vaginal cavity.

The compositions may be used both for treatment of trichomoniasis and for prevention, in case of recurrent infections. The dosage of the active ingredients: monoclonal antibody and exogenous source of complement will depend on the form of administration and on the severity of the infections state of the patient. Higher dosages are considered for the more severe cases.

The source of complement: human or animal serum (e.g.. guinea pig or rabbit serum) is preferably used in diluted form, but undiluted or less diluted concentrations may be formulated with the monoclonal antibody in case of severe infections. A mixture of different monoclonal antibodies may be used in the compositions together with the source of complement when it is desired to widen the range of the Trichomonas vaginalis strains to be eliminated.

Treatment of trichomoniasis may be accomplished by administering to a mammal the composition of the invention comprising a mixture of anti-*Trichomonas vaginalis* monoclonal antibody of the invention and a source of complement, together with a pharmaceutically acceptable carrier. The monoclonal antibodies of the invention may also be used for diagnostic purposes. To this end, they are formulated into compositions together with a diagnostically acceptable carrier. These compositions are used in a diagnostic method wherein a sample from the host suspected to suffer from trichomoniasis, is contacted with the diagnostic composition of the invention and the antigen-antibody interaction is measured by any known method.

The foregoing description and examples were presented in connection with certain preferred embodiments of the invention, but are not intended to limit the scope thereof. It is apparent to those skilled in the art that many modifications and changes may be made without departing from the essence of the invention, and it is contemplated that to any alternative, modification or equivalent may be included in the scope of the invention as defined in the claims herein.

We claim:

1. An anti-*Trichomonas vaginalis* monoclonal antibody of the subclass $IgG_3$ which:
   (a) fixes complement;
   (b) lyses *Trichomonas vaginalis* in the presence of exogenous complement; and,
   (c) agglutinates but does not lyse *Trichomonas vaginalis* in the absence of exogenous complement.

2. A monoclonal antibody which is produced from hybridoma cell line designated TV 1/315.10 having C.N.C.M. Accession No. I-593.

3. Hybridoma cell line designated TV 1/315.10 having C.N.C.M. Accession No. I-593.

4. A pharmaceutical composition for local administration comprising an anti-*Trichomonas vaginalis* monoclonal antibody of the subclass $IgG_3$ which
   (a) fixes complement
   (b) lyses *Trichomonas vaginalis* in the presence of exogenous complement; and
   (c) agglutinates but does not lyse *Trichomonas vaginalis* in the absence of exogenous complement;
   exogenous complement and a pharmaceutically acceptable carrier.

5. A composition according to claim 4 comprising the monoclonal antibody produced from the hybridoma cell line designated TV 1/315.10 having C.N.C.M. Accession No. I-593.

6. A composition according to claim 4 wherein said exogenous complement is derived from human serum.

7. A composition according to claim 4 wherein said exogenous complement is derived from animal serum.

8. A composition according to claim 7 wherein said animal serum is rabbit serum.

9. A composition according to claim 7 wherein said animal serum is guinea pig serum.

10. A composition according to claim 4 in a form for intravaginal administration.

11. A composition according to claim 10 in a form selected from tampon, suppository, vaginal tablet, or douche.

12. A composition according to claim 4 in a form for topical administration.

13. A composition according to claim 12 in a form selected from jelly, cream, ointment, or spray.

* * * * *